United States Patent
Komatsu et al.

(10) Patent No.: US 6,782,340 B1
(45) Date of Patent: Aug. 24, 2004

(54) BODY COMPOSITION MEASURING APPARATUS WITH BUILT-IN WEIGHT METER

(75) Inventors: Yoshichika Komatsu, Senboku-Machi (JP); Yoshitsugu Sasaki, Wako (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/686,813

(22) Filed: Oct. 12, 2000

(30) Foreign Application Priority Data

Oct. 12, 1999 (JP) .......................................... 11-290034

(51) Int. Cl.[7] .................... G01G 17/00; G01G 19/00; G01G 7/00
(52) U.S. Cl. .................................................. 702/173
(58) Field of Search ............................... 702/173, 127, 702/101, 129; 600/547, 372, 382, 384, 546, 554

(56) References Cited

U.S. PATENT DOCUMENTS

| | | | | |
|---|---|---|---|---|
| 4,947,862 A | * | 8/1990 | Kelly ........................... | 600/547 |
| 5,335,667 A | * | 8/1994 | Cha et al. .................... | 600/547 |
| 5,579,782 A | * | 12/1996 | Masuo ......................... | 600/382 |

FOREIGN PATENT DOCUMENTS

| | | | | |
|---|---|---|---|---|
| EP | 545014 A1 | * | 6/1993 | ............ A61B/5/05 |
| FR | 2698779 | | 6/1994 | |
| JP | 11113871 | | 4/1999 | |

* cited by examiner

*Primary Examiner*—Michael Nghiem
(74) *Attorney, Agent, or Firm*—McDermott, Will & Emery

(57) ABSTRACT

Disclosed is a body composition measuring apparatus based on bioelectiical impedance measurement in which a person under test can set the required personal body information with higher visibility for setting operation, while talking easy pose. At first, a no-load weight meter output or zero-point is determined immediately after power up of the apparatus. Then a person under test gets on the weight meter to conduct the weight measurement. The person under test enters or sets the personal body information such as height, sex, and age, while standing on the weight meter. Thereafter, the apparatus measures the bioelectrical impedance and calculates the body fat percentage and the fat mass of the person under test, based on the measured impedance and weight as well as the stored personal body information. Finally the apparatus displays the resultant value on a display.

8 Claims, 5 Drawing Sheets

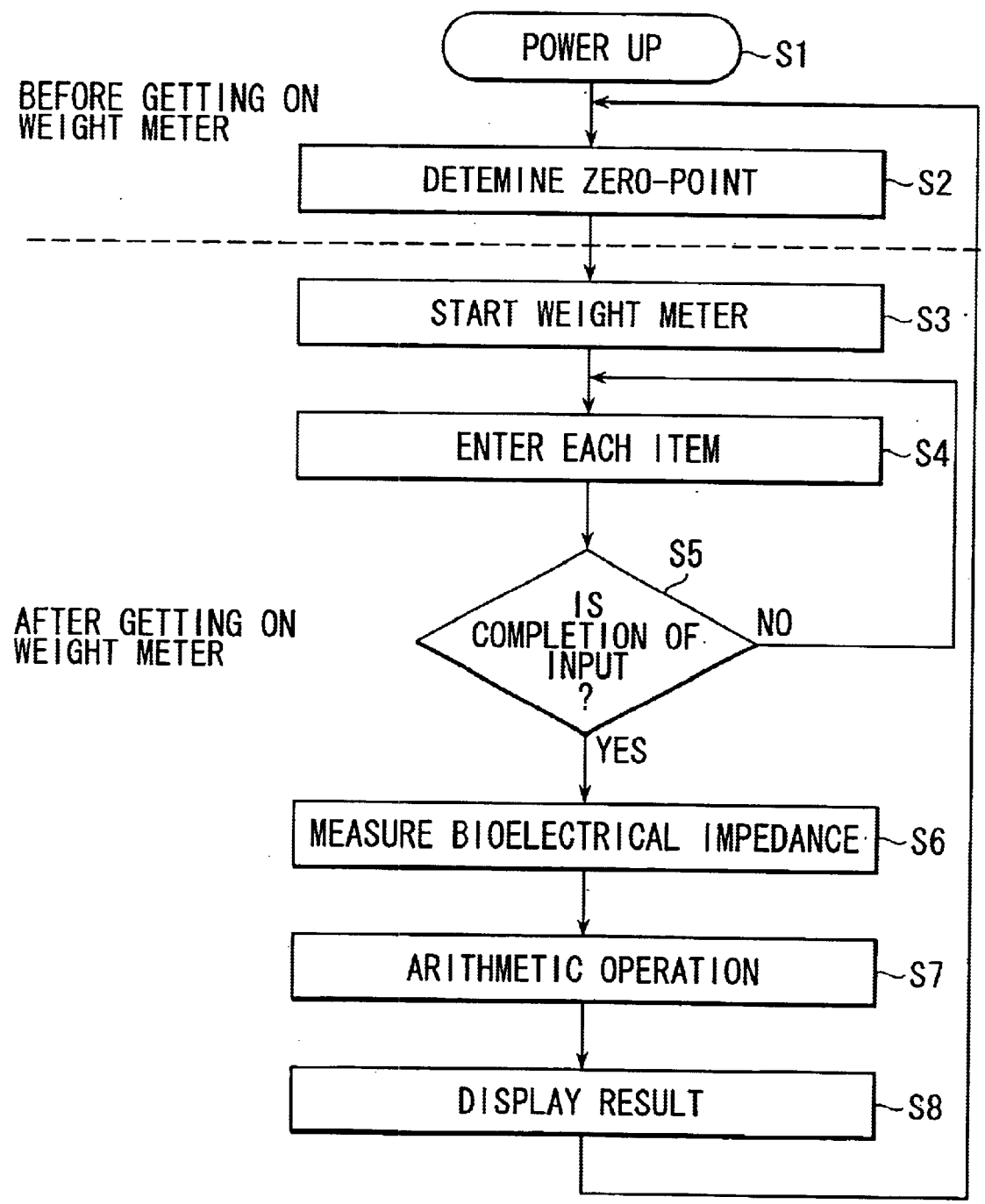

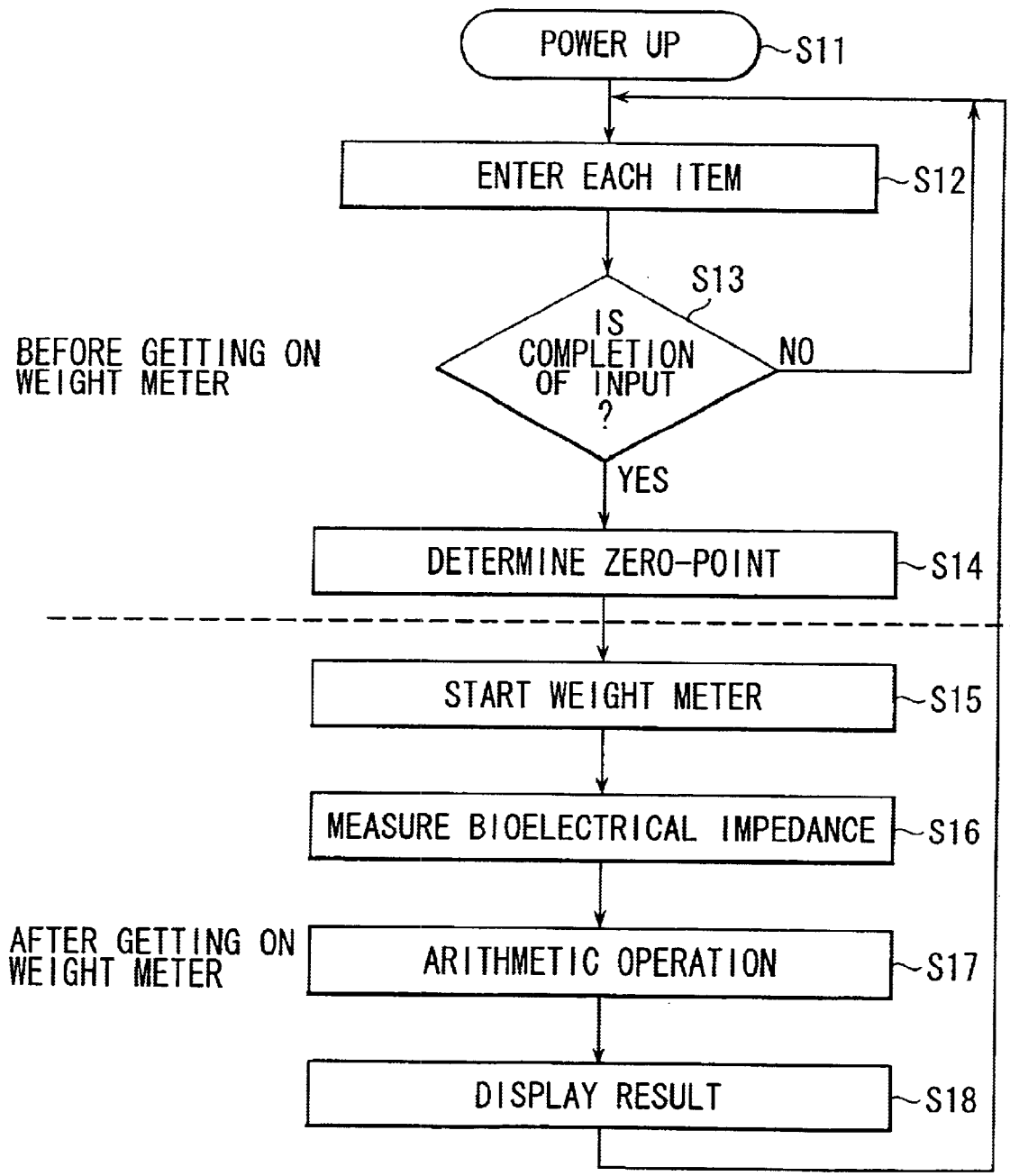

BODY COMPOSITION MEASURING APPARATUS WITH BUILT-IN WEIGHT METER

BACKGROUND OF THE INVENTION

1. Field of the Invention

The present invention relates to an apparatus for measuring body composition of a human body based on bioelectrical impedance measurement, and more particularly, to setting of a personal body information in a measuring apparatus for measuring the living body information for a person under test based on bioelectrical impedance measurement. The living body information includes, among others, a body fat percentage representing a rate of fat relative to the total weight of the person and a fat mass representing the weight of the fat.

2. Description of the Prior Art

It is already known to estimate body composition of a human body from the measurement of living body impedance. For instance, it has been found in an article "Assessment of fat-free mass using bioelectrical impedance measurement of the human body", *The American Journal of Clinical Nutrition*, 41 (4) 810–817, 1985. This principle of operation may be applied to measure the fat mass for a person under test. For instance, any impedance between extreme parts of the person such as hands and feet may be measured according to four-terminal electrode measurement theory. The impedance thus measured, together with the personal body information such as the weight, height, sex and age of the person under test, can be used to estimate the amount of body water and the fat mass for the person. For instance, (Examined) Patent Publication H5-49050 discloses apparatus for measuring the weight of a person under test concurrent with fat mass. Various types of apparatus utilizing this principle have already been put into the market.

A body composition measuring apparatus based on such bioelectrical impedance measurement is constructed such that electrodes directly contact the skin of a person under test. Then very small AC current is actually passed through the body of the person for measuring the bioelectrical impedance of the person. Then the body fat percentage and the fat mass for the person is determined from the measured bioelectrical impedance and the preset personal body information. In this regard, the personal body information is essential data and it is usually entered before starting the measurement operation.

FIG. 4 of the accompanying drawings shows one example of the case where a person under test enters the personal body information into a conventional body composition measuring apparatus with a built-in weight meter. More particularly, FIG. 4(a) shows the case where the person stands in front of the measuring apparatus for the purpose of entering the personal body information by operating a setting switch 88. FIG. 4(b) shows the case where the person stands at the side of the measuring apparatus for the same purpose. The setting switch 88 may be any conventional LCD touch panel and display in which data may be entered by operating the switch displayed on the LCD.

FIG. 5 is a flow chart representing a sequence of measuring steps for the conventional body composition measuring apparatus with a built-in weight meter. In step S11 a person under test pushes a power switch to power up the measuring apparatus. In step S12 the person enters the personal body information such as height, sex, age, etc. into the apparatus, as shown in FIG. 4. Then in step S13 confirmation is made as to whether setting of all the personal body information is completed or not. If not, the procedure restores to the data input step. After completion of setting all the persona body information, a no-load output or a zero-point is determined and stored in a weighing section of the weight meter, in step S14. The operations described above are performed before the person under test gets on the weight meter.

When the person under test gets on the weight meter and the measuring apparatus detects the load, the apparatus starts the measurement of the weight of the person, in step S15. After completion of the weight measurement, the person grasps a handgrip to measure the bioelectrical impedance for the person, in step S16. Then the apparatus calculates the body fat percentage or the fat mass for the person, based upon the measured bioelectrical impedance and the weight as well as the preset personal body information, in step S17. Thereafter, the resultant values are displayed on the display 88, in step S18.

As described above, in the conventional body composition measuring apparatus with the built-in weight meter, no load should be applied to the weight meter up to the time that the personal body information is entered and the zero-point or the no-load weight meter output is determined. Therefore, only after the completion of entering or setting the personal body information by the person who does not get on the weight meter, the conventional measuring apparatus can operate to measure the weight and then the bioelectrical impedance for the person.

The way of entering the personal body information, as conducted in the conventional body composition measuring apparatus with the built-in weight meter, has several deficiencies. Referring first to FIG. 4(a), due to the fact that the person stands in front of the measuring apparatus for entering such personal information, and has relatively longer distance to the setting switch 88, the person unavoidably takes unnatural pose such as bending his waist or stretching his arm. This leads to a big burden imposed to the person if he is an aged person or a child, or a patient.

Then referring to FIG. 4(b), because of the person standing at the lateral side of the measuring apparatus for entering the personal information, there is less burden as described above imposed to the person. However, the person should watch the setting switch 88 from the lateral side thereof. In view of the viewing angle designed for LCD, the person has the most visibility to watch the LCD at the position directly opposed to it or within the angle of several degrees offset therefrom. At the positions directly over or beneath the LCD, or at the positions lateral or oblique to the LCD, however, it is difficult for the person to watch the LCD or it may happen that the person can not perceive the LCD being ON at all. This is not limited to the touch panel with LCD, but the same is true for all the common LCD.

Accordingly, in the case as shown in FIG. 4(b), in order to enter the personal information, the person should move his face to the position opposite to the LCD or stretch his back to get better visibility to the LCD. Such action is very cumbersome for the person.

Especially, when entering the parameters that may greatly vary depending on the persons under test, such as height, etc., it takes longer period of time for entering them, and the unnatural pose required during such period of time, of course, imposes greater burden to the person.

In addition, in the conventional body composition measuring apparatus with the built-in weight meter, the person gets on the weight meter after entering the personal body information, as described above. Therefore, if any variation in amount of body water is produced due to any movement of the body immediately before the measurement, it may affect the measurement of body composition.

In view of the above, an object of the present invention is to provide a new and improved body composition measuring apparatus based on bioelectrical impedance measurement in which a person under test can set the required personal body information with higher visibility for setting operation, while taking easy pose. Another object of the present invention is to reduce any introduction of error factors into the body composition measurement.

SUMMARY OF THE INVENTION

To attain those objects, the present invention provides a body composition measuring apparatus with a built-in weight meter based on bioelectrical impedance measurement, comprising.

a weight meter;

a data input device;

an impedance measurement device; and a CPU, whereby said CPU estimates the body composition for the person under test based upon the data from said weight meter, said data input device, and said impedance measurement device, characterized in that said weight meter taking in a no-load output thereof immediately after power up of said apparatus; and personal body information is entered using said data input device after measuring the weight.

Preferably, said body composition is at least one of the following: the body fat percentage, the fat mass, the amount of body water and the amount of muscle.

This invention will now be described in further detail with regard to the preferred embodiments as illustrated in the accompanying drawings.

BRIEF DESCRIPTION OF THE DRAWINGS

FIG. 2 is a flow chart representing a sequence of operation steps for the body composition measuring apparatus;

FIG. 5 is a flow chart representing a sequence of operation steps for the conventional body composition measuring apparatus.

DESCRIPTION OF THE PREFERRED EMBODIMENTS

In a body composition measuring apparatus with a built-in weight meter according to the present invention, a no-load weight meter output or a zero-point is first determined immediately after power up of the apparatus. Then a person under test gets on the weight meter to conduct the weight measurement. The person under test enters or sets the personal body information such as height, sex, and age, while standing on the weight meter. Thereafter, the apparatus measures the bioelectrical impedance and calculates the body fat percentage and the fat mass of the person under test, based on the measured impedance and weight as well as the stored personal body information. Finally the apparatus displays the resultant value on a display.

Now the present invention will be described in more detail with reference to the accompanying drawings.

Figure 1:
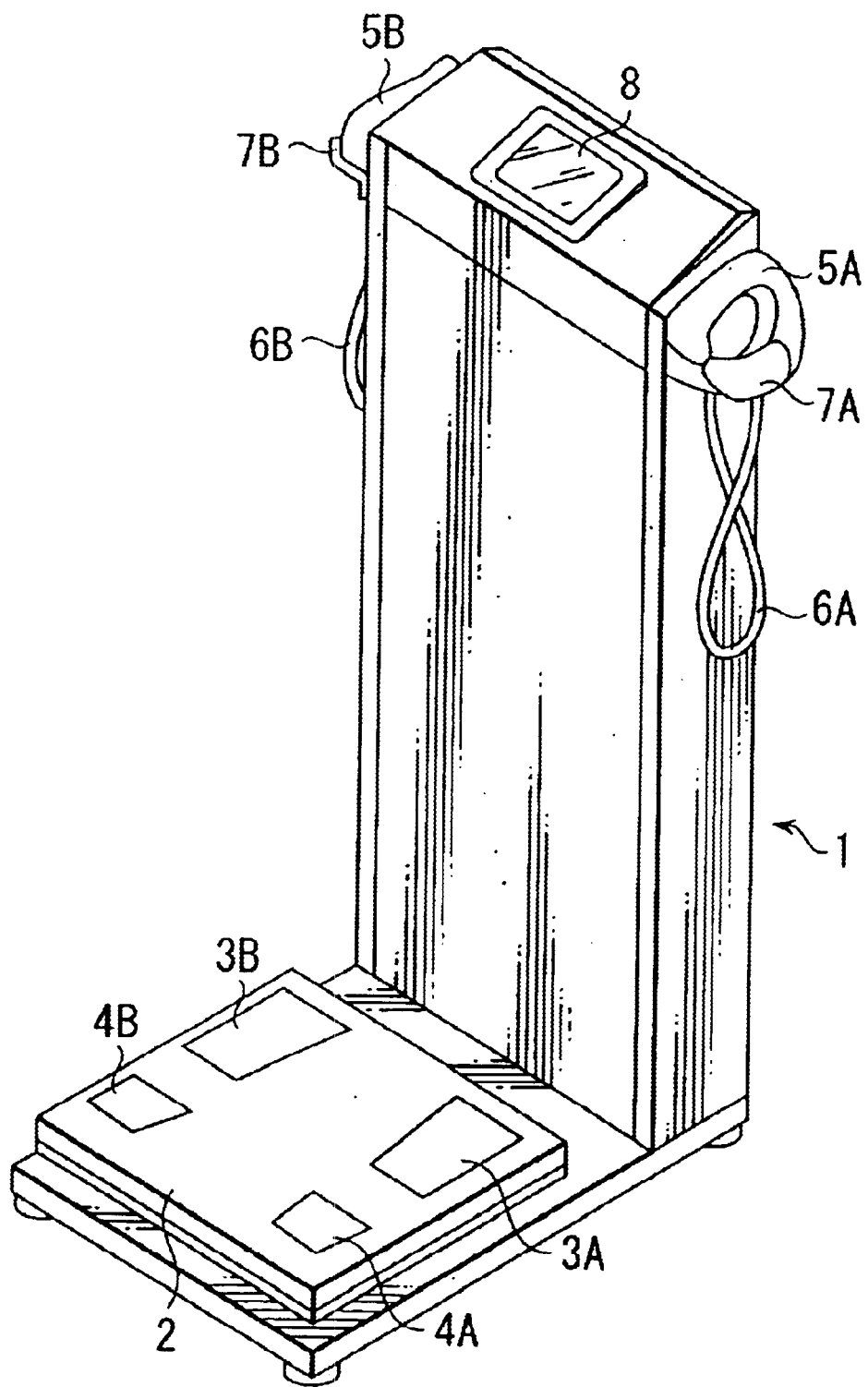
FIG. 1 is a perspective view representing a body composition measuring apparatus with a built in weight meter according to the present invention.

FIG. 1 is a perspective view representing a body composition measuring apparatus 1 operated based on a biological impedance measurement according to the present invevtion. The body composition measuring apparatus 1 is provided with hand electrodes and foot electrodes for measuring the impedance for a whole body of the person. The body composition measuring apparatus 1 include an "L" shaped body comprising vertical and horizontal portions. A conventional weight meter 2 is mounted on the horizontal portion of the body composition measuring apparatus 1. The weight meter 2 includes foot electrodes 3A, 3B, 4A and 4B on the measuring plane thereof These foot electrodes are arranged to contact with soles of a person under test when performing the measurement. More specifically, the foot electrode 3A is contact with a toe of the right foot, and the foot electrode 3B is contact with a toe of the left foot of the person. Further the foot electrode 4A is contact with a heel of the right foot, and the foot electrode 4B is contact with a heel of the left foot of the person. The electrodes 3A and 3B act to supply an electric current to the body of the person under test. The electrodes 4A and 4B are used as voltage measurement electrodes for bioelectrical impedance measurement.

The body composition measuring apparatus 1 further includes a right-hand-handgrip 5A and a left-hand-handgrip 5B held on the opposite sides of the vertical portion. The handgrips 5A and 5B are connected to the apparatus 1 via electric wires 6A and 6B, respectively. In addition, grip holders 7A and 7B are mounted on the apparatus 1 for holding the handgrips 5A and 5B, respectively. The grip holders are mainly used to hold the handgrips during the time period other than that for the bioelectrical. impedance measurement.

Further, a display 8 is mounted on the top of the body composition measuring apparatus 1. The display 8 is formed by an LCD module with a touch panel (hereafter referred to as simply a "touch panel"). In addition to displaying the measurement result, personal information and waiting message, the display 8 has a data input function with the aid of the touch panel. Therefore, it is possible to enter the information such as height, sex, and age of the person under test and to enter other information by pushing some switches displayed on the touch panel.

The circuit configuration of the body composition measuring apparatus 1 based upon the bioelectrical impedance measurement is not described here in detail, because it is already known in the art. It is sufficient to say that the body composition measuring apparatus 1 includes a CPU for performing a various kind of arithmetic operations and control functions, and a constant current source for producing a constant current or a measuring current in response to the instruction from the CPU. The constant current source is connected at its output terminals to the current supplying foot electrodes 3A, 3B and to the current supplying electrodes for hands mounted on the handgrips 5A, 5B.

The voltage measuring electrodes 4A, 4B and the voltage measuring electrodes mounted on the handgrips 5A, 5B are connected to a voltage amplifier circuit in the body composition measuring apparatus 1. The apparatus 1 further includes detection circuit for shaping the amplified voltage signal, and an A/D converter for converting the shaped, amplified voltage signal from analog form to digital form.

The converted digital signal from the A/D converter is entered into the CPU. A weight sensor of the weight meter 2 is also connected to the CPU for calculating the weight value.

Also connected to the CPU is the display 8. This is formed by an LCD with a touch panel. The display 8 generally displays the body composition information such as the body fat percentage and the fat mass, as estimated based upon the bioelectrical impedance value and the weight value measured as well as the preset and stored personal information of the person under test. The display 8 also has the switching function on the touch panel. Accordingly the CPU calculates the bioelectrical impedance based on the measuring current fed into the body of the person and the voltage actually measured. Then the CPU estimates the body fat percentage and the fat mass from the calculated bioelectrical impedance value and the weight value, as well as the stored personal information, and thereafter, displays them on the display 8.

Then the sequence of operation steps for the body composition measuring apparatus will be described with reference to FIGS. 2 and 3. FIG. 2 is a flow chart representing a measuring sequence, and FIG. 3 shows a setting operation, by way of example. In step 1 the person under test pushes a measurement start switch on the touch panel to power up the measuring apparatus. Immediately after the power up, the measuring apparatus determines and stores a zero-point or a no-load weight meter output, in step S2.

Figure 3C:
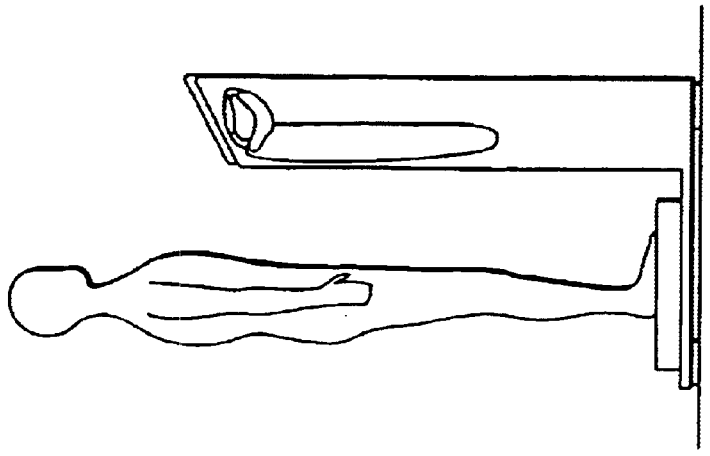
FIG. 3 is a view representing the measuring sequence for the body composition measuring apparatus.
Figure 3B:
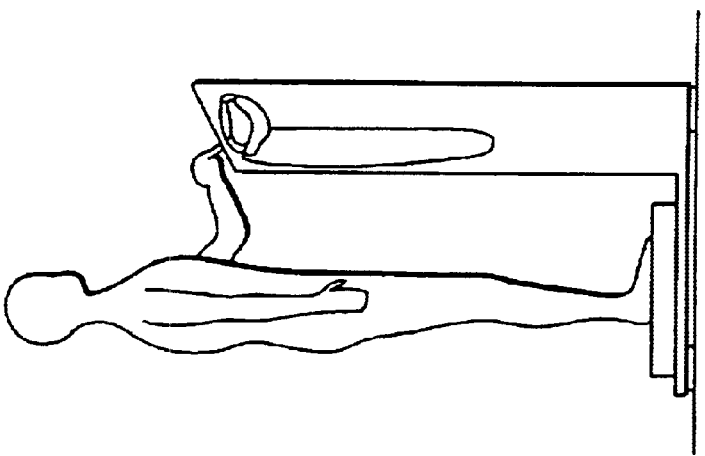
Figure 3A:
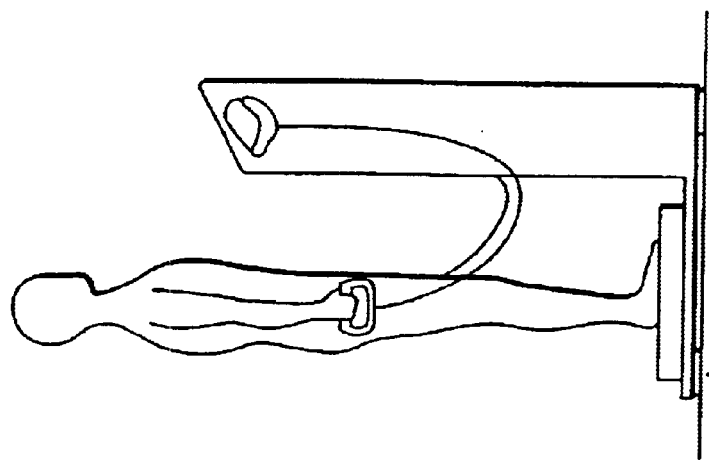
Figure 4A:
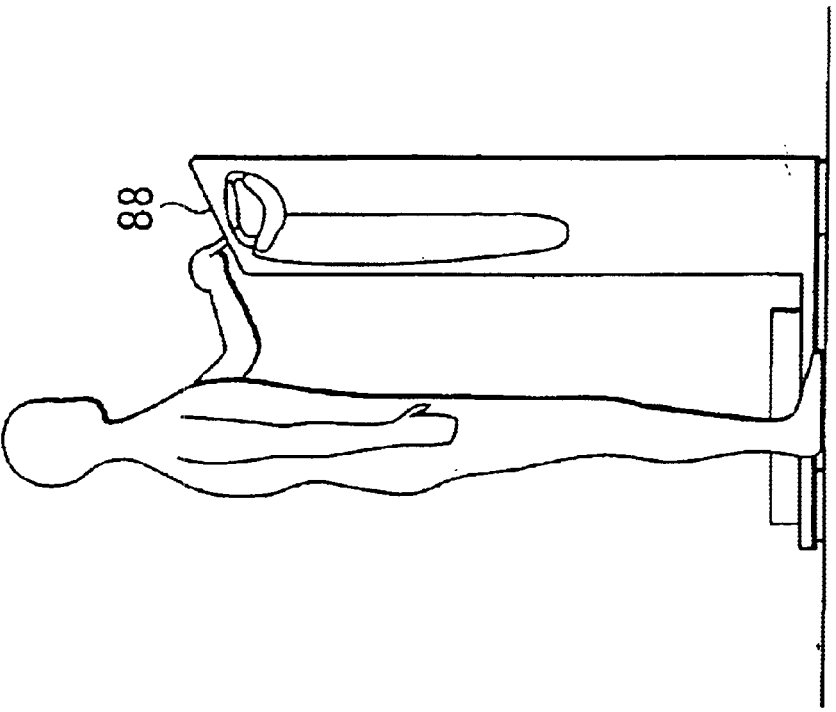
FIG. 4 is a view representing the condition wherein the setting of the personal body information is performed in a conventional body composition measuring apparatus with a built in weight meter.
Figure 4B:
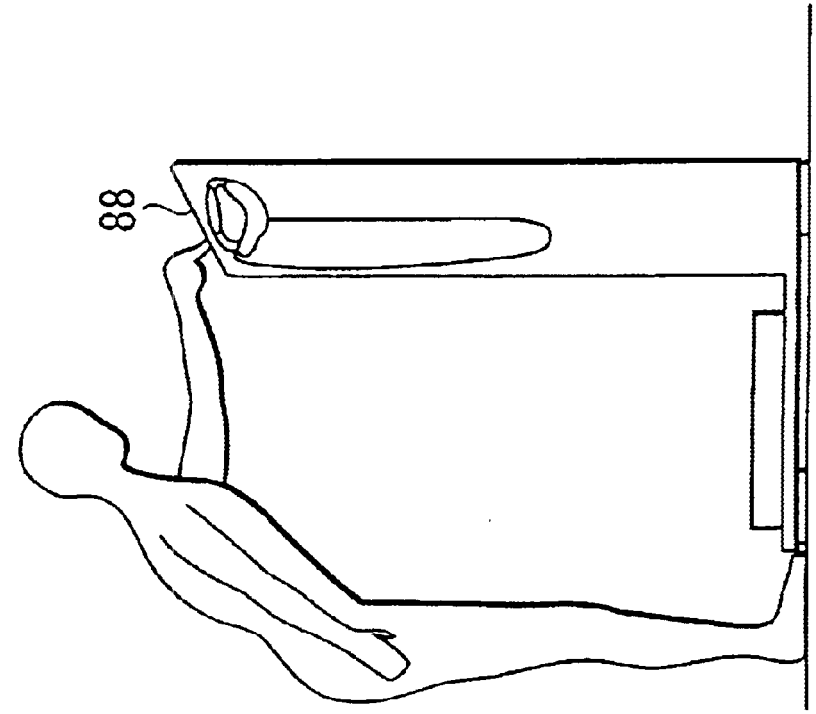

Then the person under test gets on the weight meter 2 on the body composition measuring apparatus 1 with his soles making contact with the foot electrodes thereon. Such condition is illustrated in FIG. 3(a). At this time, the toe and heal of right foot of the person are in contact with the current supplying electrode 3A and the voltage measurement electrode 4A, respectively. Similarly, the toe and heal of left foot of the person are in contact with the current supplying electrode 3B and the voltage measurement electrode 4B, respectively. When detecting the load, the measuring apparatus starts to measure the weight of the person, in step S3. The weight value measured is then stored.

After completion of the weight measurement, the procedure enters a personal body information input mode. While standing on the weight meter, the person under test sequentially enters or sets the personal body information such as height, sex and age using the touch panel on the display 8, in step S4. Such condition is illustrated in FIG. 3(b). It is noted, here, that the person can enter such information while standing on the weight meter, other than standing in front of or at the lateral side of the measuring apparatus, as in the previous case. This is the best condition for entering the information in that the person can see the touch panel screen at the position directly opposed to it and can take easy pose due to the shorter distance to the switch.

Thereafter, in step S5, confirmation is made as to whether the setting of all the personal body information is completed or not. If not, the procedure restores to the data input step.

After the completion of entering all the personal body information, the display 8 shows a message indicating that the handgrips 5A and 5B should be grasped. Then the person under test picks up the handgrips 5A and 5B held in the grip holders 7A and 7B with his right and left hands, respectively. Now, the handgrips 5A and 5B are grasped with the hands of the person with his palms in contact with the current supplying and voltage measurement electrodes. Thereafter, the person naturally drops down both arms to take a pose for measurement, thereby starting the measurement, in step S6. FIG. 3(c) shows the condition in which the measurement of bioelectrical impedance is conducted.

In step S7 the body fat percentage or the fat mass is calculated by CPU based on the measured bioelectrical impedance and the weight as well as the preset personal body information. Then in step S8 the resultant value is displayed on the display 8.

In the above description, the present invention has been described as regard to the body composition measuring apparatus in which the foot electrodes on the weight meter are used in combination with the hand electrodes for allowing the measurement of whole body and/or any parts of the person. However, the present invention is not limited to any specified number of, or any specified construction of the electrodes, or to any specified positions on the body with which they are placed, because the present invention is directed toward how to input the required information to the measuring apparatus.

Furthermore, the present invention has been described as regard to the case where the body composition that can be estimated is the body fat. However, the body composition that can be estimated further includes the amount of body water and the amount of muscle.

In the body composition measuring apparatus with the built-in weight meter according to the present invention, at first a person under test gets on the weight meter for measuring the weight and then he enters or sets the personal body information while standing on the weight meter. Therefore, the person can confirm the touch panel screen at the position directly opposed to it so that good viewing angle can be attained. In addition, the person can take easy pose for entering or setting the personal information due to the shorter distance to the switch.

Accordingly, there is no need for the person to take unnatural pose such as bending his waist or stretching his arm. This greatly relieves the burden imposed to the person if he is an aged person or a child, or a patient, and makes the measuring apparatus very convenient for the user.

When the body composition measuring apparatus with the built-in weight meter according to the present invention is used to measure the body composition for the person under test, all the necessary operations including measurement of the weight, input of the personal body information and measurement of the body fat percentage can be performed while the person stands on the weight meter. The only action required for the person is movement of his hands. Therefore, there is less transfer of the body water produced in the body of the person. This contributes to reduce the error factors in measurement and to allow higher precision measurement of the body composition.

What is claimed is:

1. A body composition measuring apparatus with a built-in weight meter based on bioelectrical impedance measurement, comprising:

a weight meter for measuring a weight of a person under test;

a data input device;

an impedance measurement device; and a CPU, wherein personal body information is entered using said data input device while the person under test stands on said weight meter after measuring the weight;

a weight sensor of said weight meter is connected to said CPU; and said CPU estimates the body composition of the person under test based upon the personal body information, the weight measured prior to entering the personal body information, and data from said impedance measurement device.

2. A body composition measuring apparatus with a built-in weight meter based on bioelectrical impedance measurement comprising:
   a weight meter for measuring a weight of a person under test;
   a data input device;
   an impedance measurement device; and
   a CPU, wherein
   said weight meter determines a no-load output thereof immediately after power up of said apparatus;
   personal body information is entered using said data input device while the person under test stands on said weight meter after measuring the weight;
   a weight sensor of said weight meter is connected to said CPU; and
   said CPU estimates the body composition of the person under test based upon an output of said weight meter and data from said input device and said impedance measurement device.

3. A body composition measuring apparatus with a built-in weight meter according to claim 1 or 2 wherein said weight meter measures the weight in response to detecting the load.

4. A body composition measuring apparatus with a built-in weight meter according to claim 1 or 2 in which said personal body information includes at least one of the following: the height, the sex and the age of the person under test.

5. A body composition measuring apparatus with a built-in weight meter according to claim 1 or 2 in which said body composition includes at least one of the following: the body fat percentage, the fat mass, the amount of body water and the amount of muscle of the person under test.

6. A body composition measuring apparatus with a built-in weight meter according to claim 1 or 2, wherein said weight meter measures the weight in response to detecting the load, and wherein said personal body information includes at least one of the following: the height, the sex and the age of the person under test.

7. A body composition measuring apparatus with a built-in weight meter according to claim 1 or 2, wherein said weight meter measures the weight in response to detecting the load, and wherein said body composition includes at least one of the following: the body fat percentage, the fat mass, the amount of body water and the amount of muscle of the person under test.

8. A body composition measuring apparatus with a built-in weight meter according to claim 1 or 2, wherein said body composition includes at least one of the body fat percentage, the fat mass, the amount of body water and the amount of muscle of the person under test, and wherein said personal body information includes at least one of the height, the sex and the age of the person under test.

* * * * *